US007429679B2

(12) United States Patent
Lim et al.

(10) Patent No.: US 7,429,679 B2
(45) Date of Patent: Sep. 30, 2008

(54) SULPHONIC ACID SALT OF SIBUTRAMINE

(75) Inventors: Dong Kwon Lim, Gyeonggi-do (KR); Eun Young Yang, Gyeonggi-do (KR); Jae Kyoung Ko, Incheon (KR); Kwang Do Choi, Gyeonggi-do (KR); Yong Sik Youn, Gyeonggi-do (KR); Hea Ran Suh, Gyeonggi-do (KR); Chang Ju Kim, Gyeonggi-do (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 10/580,135

(22) PCT Filed: Jan. 6, 2006

(86) PCT No.: PCT/KR2006/000072

§ 371 (c)(1),
(2), (4) Date: Mar. 2, 2007

(87) PCT Pub. No.: WO2006/073291

PCT Pub. Date: Jul. 13, 2006

(65) Prior Publication Data
US 2007/0191481 A1 Aug. 16, 2007

(30) Foreign Application Priority Data
Jan. 6, 2005 (KR) ............... 10-2005-0001404

(51) Int. Cl.
*C07C 211/63* (2006.01)
*A61K 31/14* (2006.01)
(52) U.S. Cl. ............... 564/282; 564/283; 564/289; 514/650
(58) Field of Classification Search ............ None
See application file for complete search history.

(56) References Cited

U.S. PATENT DOCUMENTS

| 6,331,571 | B1 | 12/2001 | Jerussi et al. | |
|---|---|---|---|---|
| 2004/0068018 | A1* | 4/2004 | Lee et al. | 514/650 |
| 2007/0191482 | A1 | 8/2007 | Choi et al. | |
| 2007/0191489 | A1 | 8/2007 | Lim et al. | |

FOREIGN PATENT DOCUMENTS

| WO | WO 95/21615 A1 | 8/1995 |
|---|---|---|
| WO | WO 98/13034 A1 | 4/1998 |
| WO | WO 00/56310 A1 | 9/2000 |
| WO | WO 00/56313 A1 | 9/2000 |

OTHER PUBLICATIONS

Database Caplus on STN, Acc. No. 2004:690754, Athayde, Br 2001005486 (Oct. 7, 2003) (abstract).*
International Search Report for International Application No. PCT/KR2006/000072, mailed Apr. 19, 2006, Korean Intellectual Property Office, Republic of Korea.

Office Action for U.S. Appl. No. 10/580,136, Lim et al., 35 U.S.C. § 371 date: Mar. 2, 2007, International Filing Date: Jan. 6, 2006, mailed on Oct. 4, 2007.
Database Caplus, Accession No. 2004:690754, Document No. 141:179571, record for Athayde, A., "Preparation of sibutramine hydrogensulfate," Brazilian Patent Application No. 2001005486.
Database Delphion, record for Athayde, A., "Process is for obtaining sulphate of 1-(4-chlorophenyl)-N,N-dimethyl-alpha-(2-methylpropyl)-cyclobutanomethamine and its isomers," Brazllian Patent Application No. 2001000005486.
Database Caplus, Accession No. 1987:623314, Document No. 107:223314, record for Jeffrey et al., "N,N-dimethyl-1-[1-(4-chlorophenyl)cyclobutyl]-3-methylbutylamine hydrochloride monohydrate for use in treating depression," Great Britain Patent No. 2184122.
Office Action for U.S. Appl. No. 10/580,132, Choi et al., 35 U.S.C. § 371 date: May 2, 2007, International Filing Date: Jan. 6, 2006, mailed on Oct. 4, 2007.
Database Caplus, Accession No. 2004:965047, Document No. 141:400964, record and English language abstract for Lulla et al., "Pharmaceutical formulation comprising anti-obesity agent and acidulant," International Patent Application Publication No. WO2004096202.
Database Caplus, Accession No. 2001:526047, Document No. 135:122299, record and English language abstract for Senanayake et al., "Synthesis of racemic and optically pure desmethylsibutramine, didesmethylsibutramine, oral formulations comprised thereof and their use as doparmine reuptake inhibitors," International Patent Application Publication No. WO2001051453.
Database Caplus, Accession No. 2001:565912, Document No. 135:111957, record and English language abstract for Fu et al., "Preparation of monohydrate of N,N-dimethyl-1-(1-(4-chlorophenyl)cyclobutyl)-3-methylbutylamine hydrochloride," Chinese Patent No. 1125032.
Database Caplus, Accession No. 2004:690574, Document No. 141:179571, record for Athayde, A., "Preparation of sibutramine hydrogensulfate," Brazilian Patent Application No. 2001005486, (2003).
Database Delphion, record for Athayde, A., "Process is for obtaining sulphate of 1-(4-chlorophenyl)-N,N-dimethyl-alpha-(2-methylpropyl)-cyclobutanomethamine and its isomers," Brazilian Patent Application No. 2001000005486, (2003).
Database Caplus, Accession No. 1987:623314, Document No. 107:223314, record for Jeffrey et al., "N-N-dimethyl-1-[1-(4-chlorophenyl)cyclobutyl]-3-methylbutylamine hydrochloride monohydrate for use in treating depression," Great Britian Patent No. 2184122, (1987).
Database Caplus, Accession No. 2004:965047, Document No. 141:400964, record and English language abstract for Lulla et al., "Pharmaceituca formulation comprising anti-obesity agent and acidulant," International Patent Application Publication No. WO2004096202, (2004).

(Continued)

*Primary Examiner*—Brian J Davis
(74) *Attorney, Agent, or Firm*—Sterne, Kessler, Goldstein & Fox PLLC

(57) ABSTRACT

Disclosed is a novel sulphonic acid salt of sibutramine, which has good physicochemical properties. Also disclosed are a method of preparing the compound and a pharmaceutical composition comprising the compound.

10 Claims, 10 Drawing Sheets

OTHER PUBLICATIONS

Database Caplus, Accession No. 2001:526047, Document No. 135:122299, record and English language abstract for Senanayake et al., "Synthesis of racemic and optically pure desmethylsibutramine, didesmethylsibutramine, oral formulations comprised thereof and their use as dopamine reuptake inihbitors," International Patent Application Publication No. 202001051453, (2001).

Database Caplus, Accession No. 2001:565912, Document No. 135:111957, record and English language abstract for Fu et al., "Preparation of monohydrate of N,-N-dimethyl-1-(1-(4-chlorophenyl)cyclobutyl)-3-methylbutylamine hydrochloride," Chinese Patent No. 1125032, (2003).

* cited by examiner

SULPHONIC ACID SALT OF SIBUTRAMINE

TECHNICAL FIELD

The present invention relates to a novel sulphonic acid salt of sibutramine, a method of preparing the compound, and a pharmaceutical composition comprising the compound as an effective ingredient.

BACKGROUND ART

Sibutramine (N-[1-[1-(4-chlorophenyl)cyclobutyl]-3-methylbutyl]-N,N-dimethylamine), which is a inhibitor of 5-hydroxytryptamine and noradrenaline reuptake in vivo (Neuropharmacology, 28, p 129-134), is useful in the treatment of depression, Parkinson's disease, obesity, insulin-independent diabetes mellitus, epilepsy, and the like. In addition, sibutramine reduces body weight gain by a dual action to reduce food intake by enhancing satiety and to increase energy expenditure by stimulating heat generation (Int. J. Obesity, 19, p 145; Brit. J. Pharmacol. 114, p 388). The therapeutic use of sibutramine in depression is described in British Patent Specification 2098602. The therapeutic use of sibutramine in Parkinson's disease is disclosed in International Pat. Publication No. WO88/06444. The therapeutic use of sibutramine in cerebral function disorders is disclosed in U.S. Pat. No. 4,939,175. The use of sibutramine hydrochloride in the treatment of obesity is disclosed in European Pat. No. 397831. Also, International Pat. Publication No. WO95/20949 discloses the use of sibutramine for improving impaired glucose tolerance or glucose tolerance in patients suffering from insulin-independent diabetes mellitus.

Typically, the preparation of salts having pharmaceutically useful physical properties must satisfy the following physicochemical criteria: (1) good solubility, (2) good stability, (3) good non-hygroscopicity and (4) compressibility into tablet form.

Since sibutramine is difficult to purify due to its low melting point, it is preferable to use a crystalline material capable of being purified by recrystallization in order to prepare a pharmaceutical composition comprising sibutramine. Korean Pat. Publication No. 1990-0000274 discloses that sibutramine is utilized as salts formed with acids providing non-toxic acid addition salts containing pharmaceutically acceptable anions, for example, in the form of hydrochloride, malate, acetate, citrate, fumarate, tartrate, succinate, aspartate or glutamate salt.

However, since sibutramine hydrochloride is difficult to handle pharmaceutically due to its hygroscopic nature, it is undesirable to use sibutramine hydrochloride for preparing medicaments. In the preparation of medicaments, a constant weight of an active compound should be contained in each dosage form, but an active ingredient absorbing water from the surrounding environment makes it difficult to achieve such consistency. Korean Patent Publication No. 94-8913 discloses that when sibutramine hydrochloride is prepared in a monohydrate form, a non-hygroscopic product is obtained, which is suitable for the preparation of capsules, tablets and other pharmaceutical dosage forms. This patent publication describes that sibutramine hydrochloride monohydrate can be prepared by contacting sibutramine hydrochloride with a medium consisting of or containing water, which is a water-immiscible solvent or a water-miscible solvent.

The currently used sibutramine hydrochloride monohydrate is prepared using a complicated process including adding a predetermined amount of water to a reaction mixture, or including preparing sibutramine hydrochloride anhydrate and suspending the sibutramine hydrochloride anhydrate in a water-containing solvent for a long time with agitation. Also, this process is disadvantageous because it is difficult to provide a precise monohydrate being not completely hygroscopic.

In this regard, intensive and through research into the development of a novel salt of sibutramine, capable of solving the problems encountered in the prior art, conducted by the present inventors, resulted in the finding that among sulphonic acid salts of sibutramine, a benzenesulfonic acid salt (besylate), a camphorsulfonic acid salt ((+)-(1S)-camphor-10-sulfonic acid salt, camsylate), a p-toluenesulfonic acid salt (tosylate) and an ethane disulfonic acid salt (1,2-ethane disulfonic acid salt, edisylate), which are in anhydrous forms not requiring a complicated procedure for preparing a hydrate containing a certain amount of water, possess good physicochemical properties (solubility, non-hygroscopicity and stability). Also, the present inventors found that a hydrous form among sulphonic acid salts of sibutramine, an ethanesulfonic acid salt (esylate) hemihydrate has remarkably high solubility in water compared to sibutramine hydrochloride monohydrate, and also exhibit non-hygroscopicity and stability.

DISCLOSURE OF THE INVENTION

It is therefore an object of the present invention to provide a novel sulphonic acid salt of sibutramine.

It is another object of the present invention to provide a method of preparing the sulphonic acid salt of sibutramine.

It is a further object of the present invention to provide a pharmaceutical composition for treating and preventing pathological states of obesity and related disorders, comprising the sulphonic acid salt of sibutramine as an active ingredient. It is yet another object of the present invention to provide a pharmaceutical composition for treating depression, Parkinson's disease, insulin-independent diabetes mellitus or epilepsy, comprising the sulphonic acid salt of sibutramine as an active ingredient.

It is yet another object of the present invention to provide a method of treating and preventing pathological states of obesity and related disorders, and a method of treating depression, Parkinson's disease, insulin-independent diabetes mellitus or epilepsy, these methods being based on administering the pharmaceutical composition comprising the sulphonic acid salt of sibutramine as an active ingredient.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
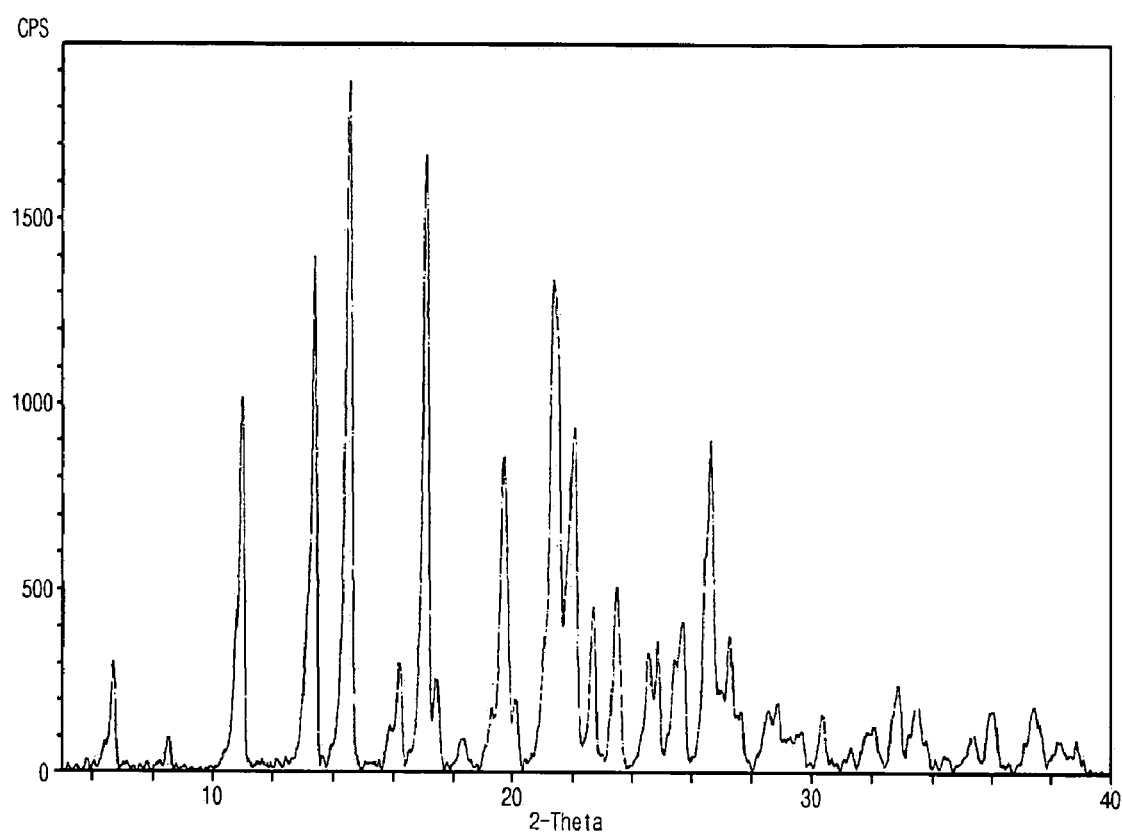
FIG. 1 is an X-ray diffraction spectrum of sibutramine besylate according to the present invention.
Figure 2:
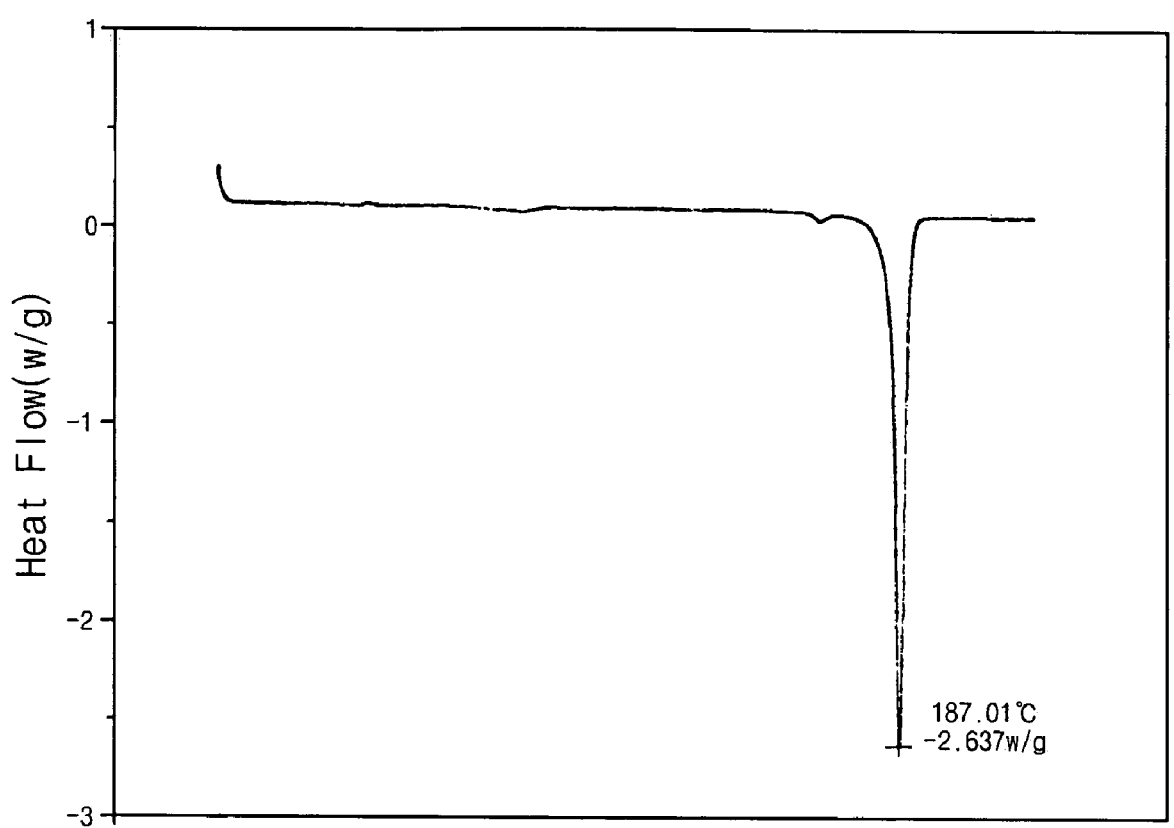
FIG. 2 is a differential scanning calorimeter thermogram of sibutramine besylate according to the present invention.
Figure 3:
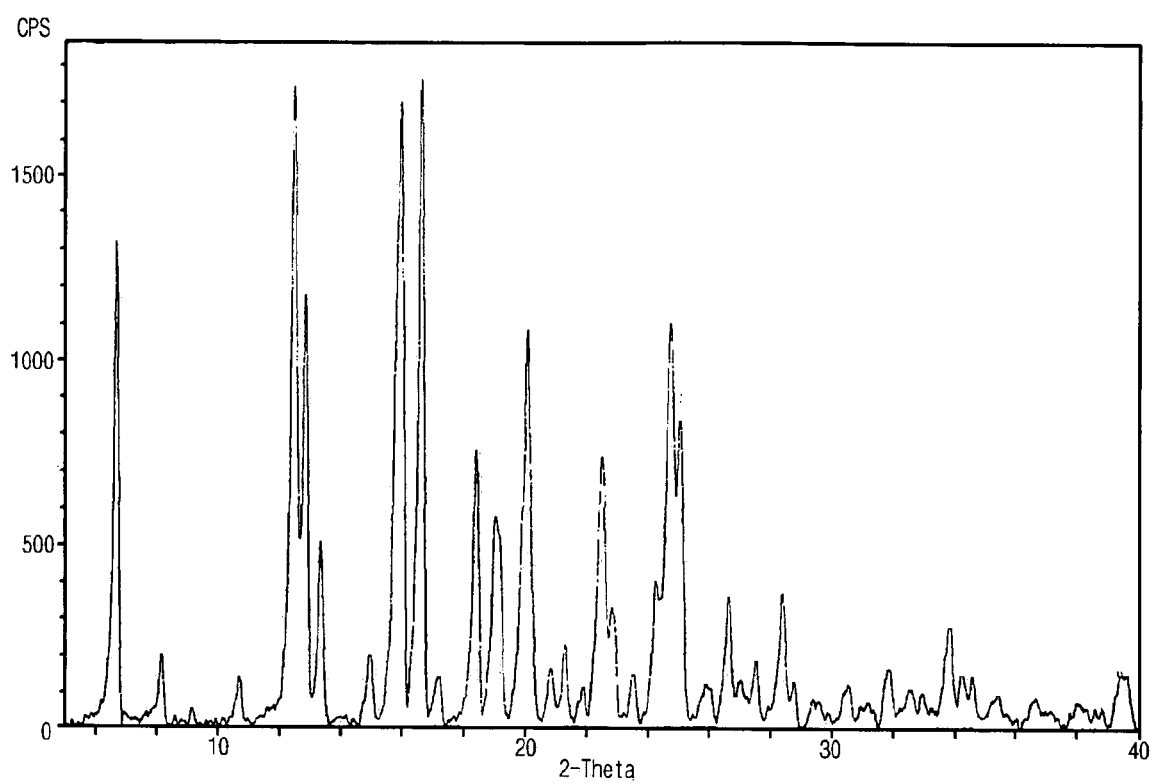
FIG. 3 is an X-ray diffraction spectrum of sibutramine camsylate according to the present invention.
Figure 4:
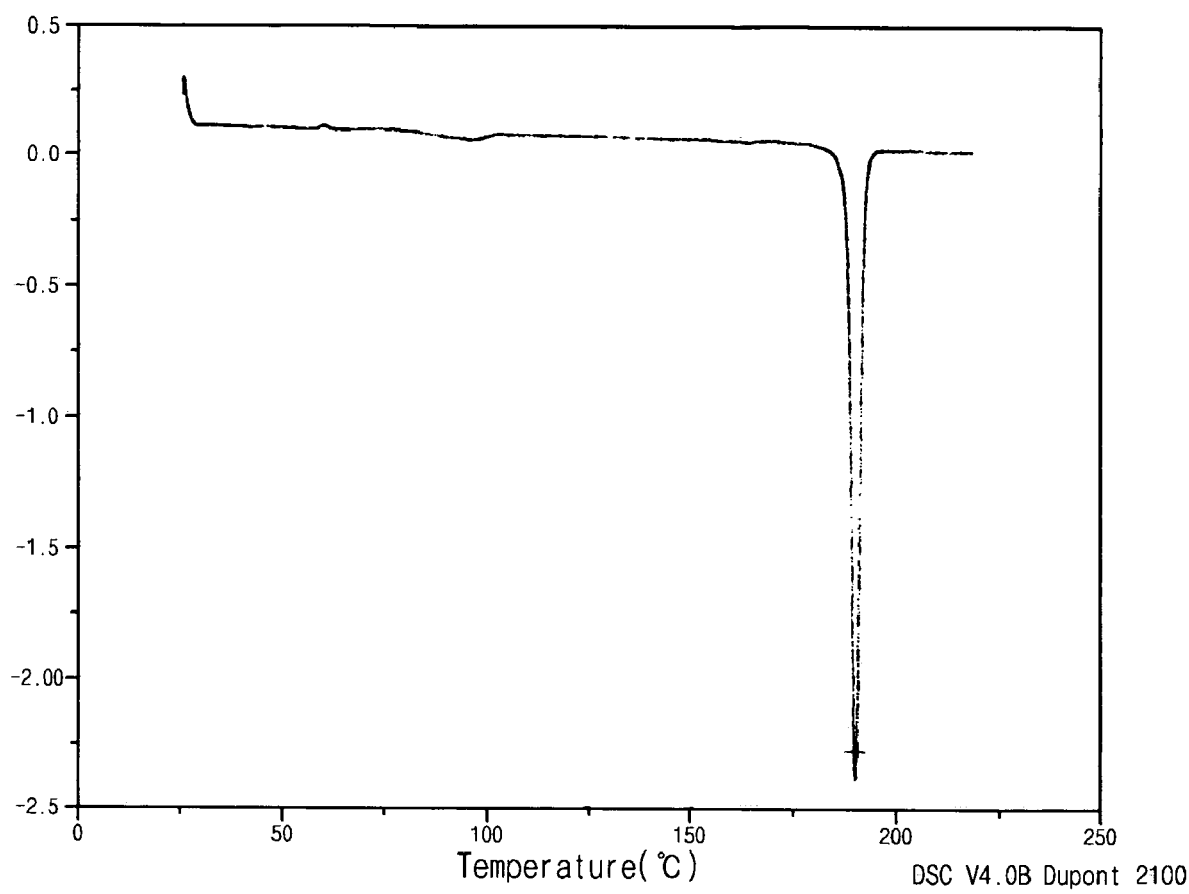
FIG. 4 is a differential scanning calorimeter thermogram of sibutramine camsylate according to the present invention.
Figure 5:
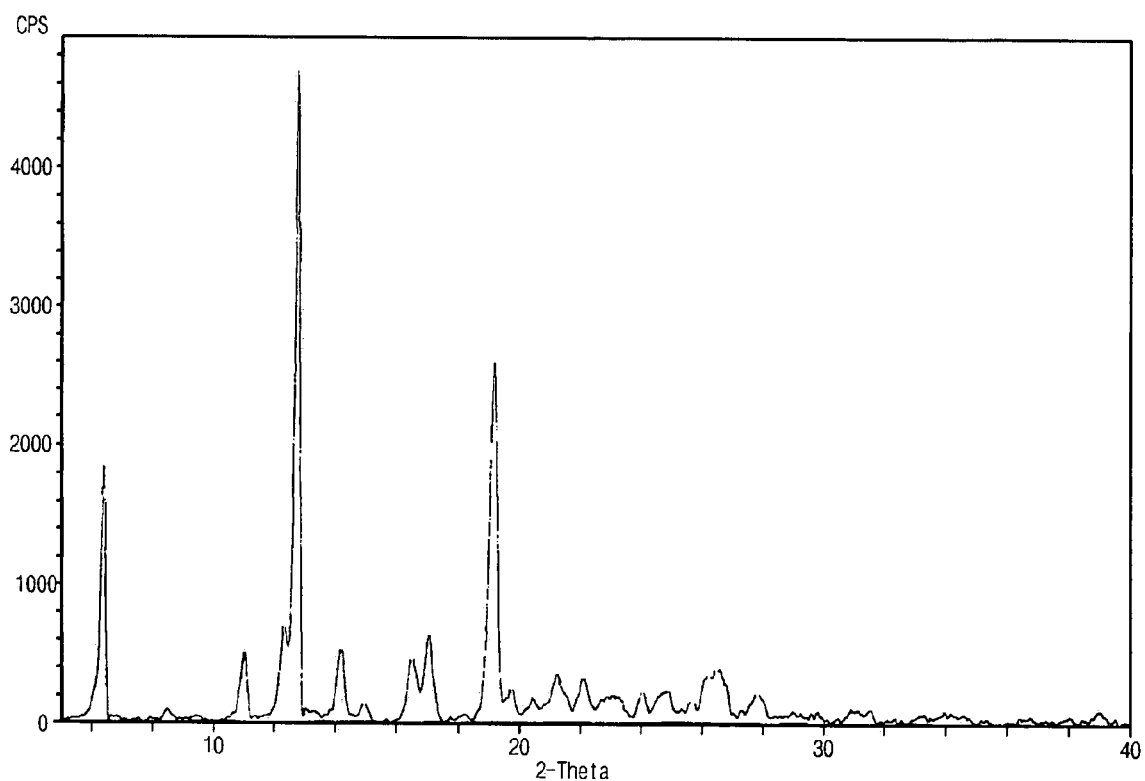
FIG. 5 is an X-ray diffraction spectrum of sibutramine tosylate according to the present invention.
Figure 6:
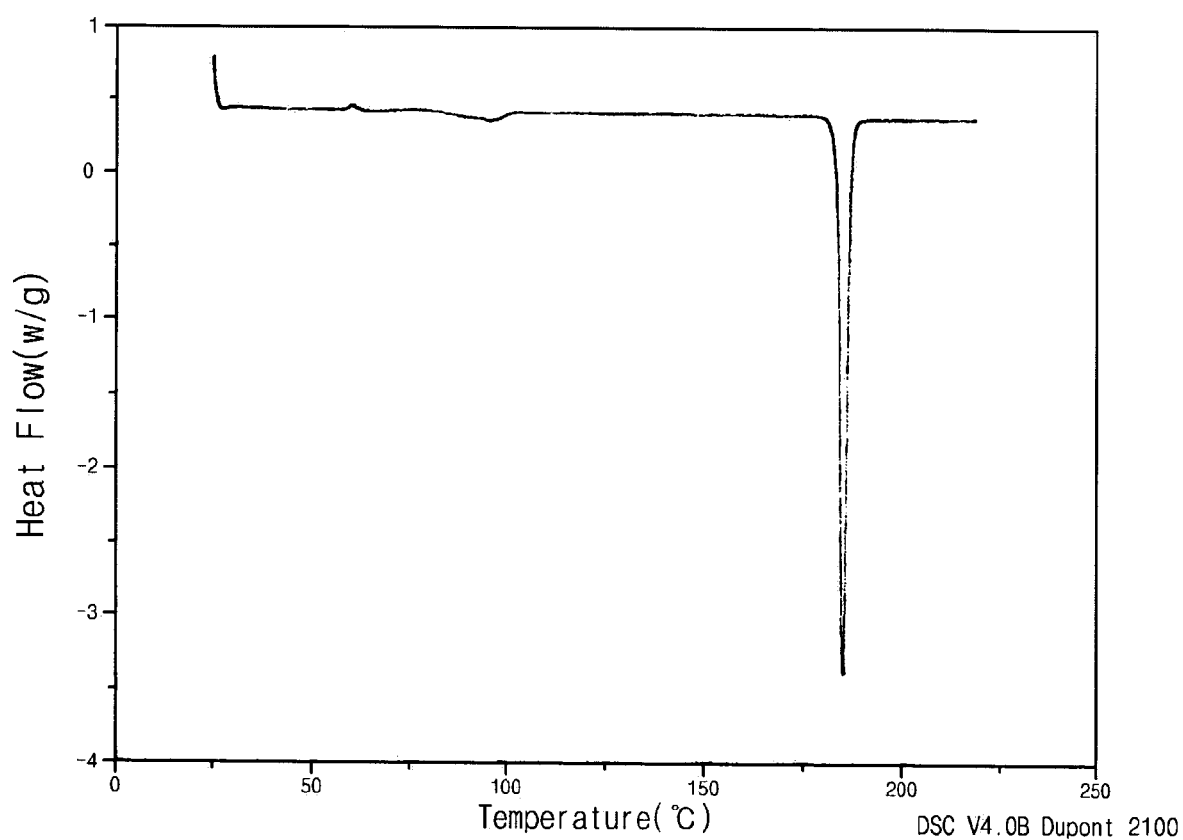
FIG. 6 is a differential scanning calorimeter thermogram of sibutramine tosylate according to the present invention.
Figure 7:
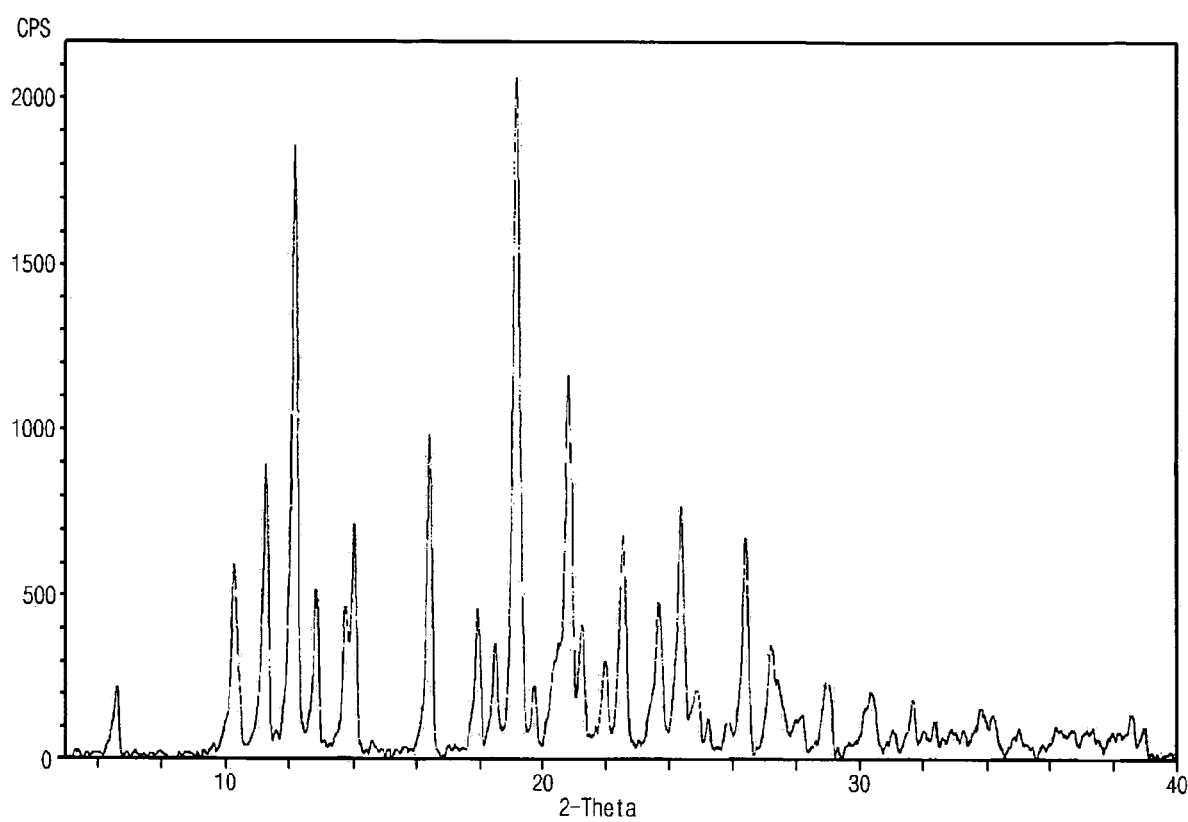
FIG. 7 is an X-ray diffraction spectrum of sibutramine edisylate according to the present invention.
Figure 8:
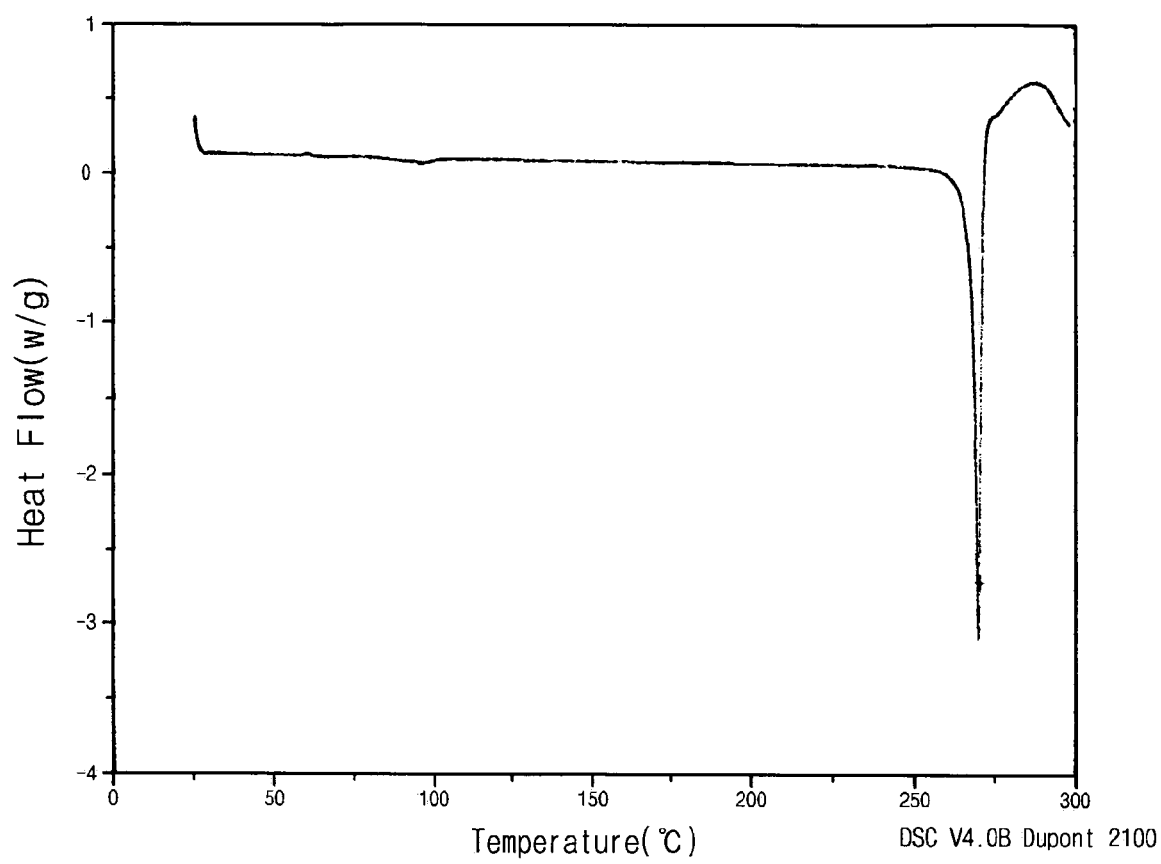
FIG. 8 is a differential scanning calorimeter thermogram of sibutramine edisylate according to the present invention.
Figure 9:
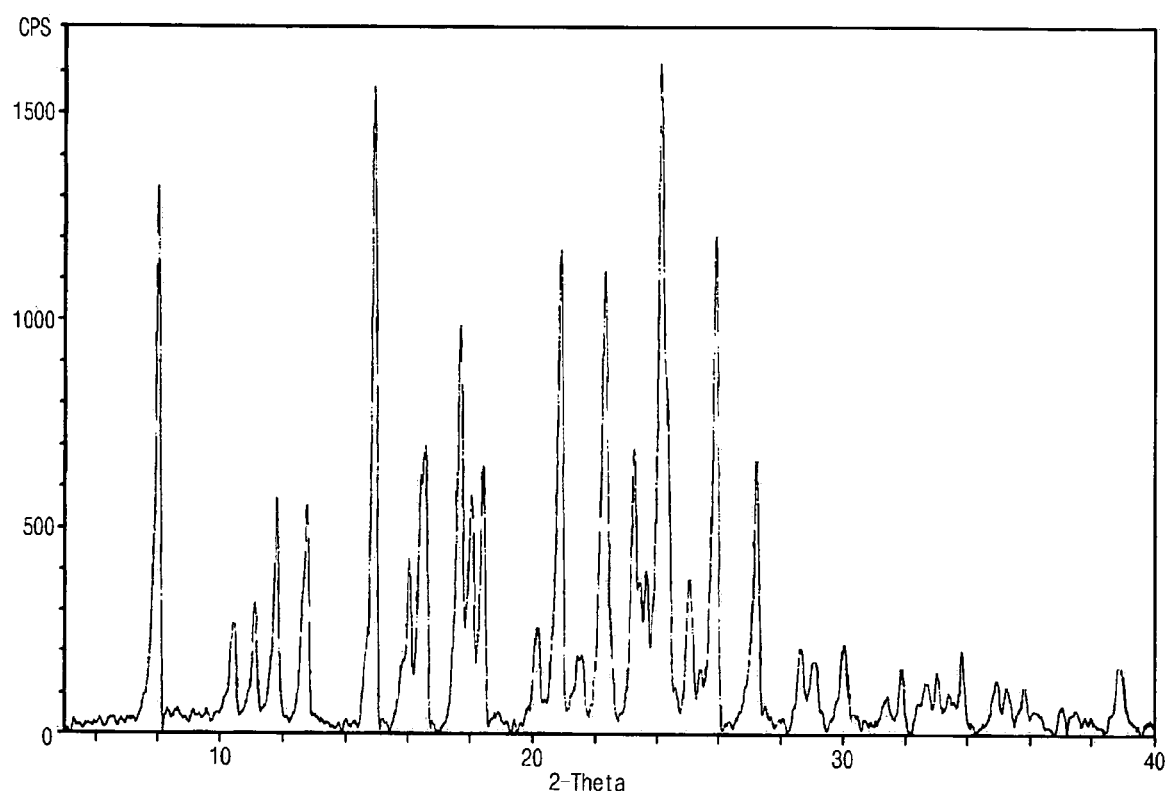
FIG. 9 is an X-ray diffraction spectrum of sibutramine esylate hemihydrate according to the present invention.
Figure 10:
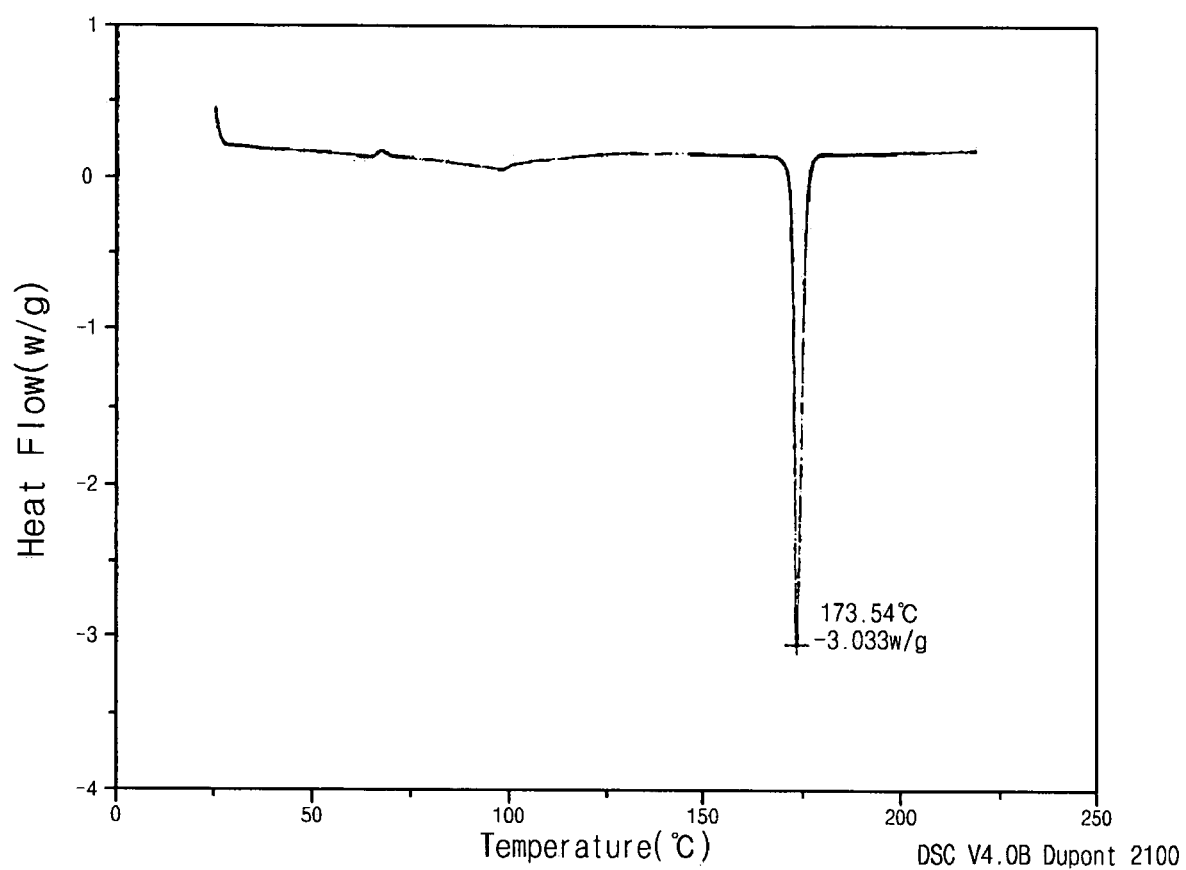
FIG. 10 is a differential scanning calorimeter thermogram of sibutramine esylate hemihydrate according to the present invention.

In one aspect, the present invention relates to a sulphonic acid salt of sibutramine, which is selected from among sibutramine besylate, sibutramine camsylate, sibutramine tosylate, sibutramine edisylate and sibutramine esylate hemihydrate.

Besylate, camsylate, tosylate, edisylate and esylate hemihydrate salts of sibutramine are represented by Chemical Formula 1, below.

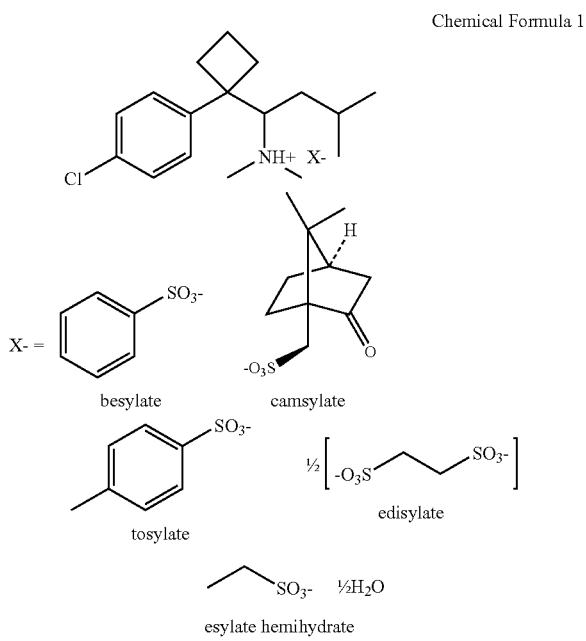

Chemical Formula 1

Besylate, tosylate and edisylate salts of sibutramine according to the present invention have non-hygroscopicity, chemical and thermodynamic stability, and formulability, identical to or better than commercially available sibutramine hydrochloride monohydrate. Also, these salt forms of sibutramine have a slightly lower solubility than sibutramine hydrochloride monohydrate, but they exhibit solubility sufficient to avoid problems with respect to pharmaceutical release or bioavailability when they are mixed with a pharmaceutically acceptable diluent or carrier to provide a pharmaceutical composition. Camsylate and esylate hemihydrate salts of sibutramine according to the present invention display solubility, non-hygroscopicity, chemical and thermodynamic stability, and formulability, identical to better than sibutramine hydrochloride monohydrate. In particular, sibutramine esylate hemihydrate exhibits an excellent solubility, two times-higher than the solubility of sibutramine hydrochloride, in distilled water and aqueous solutions of pH 1.2, pH 4.0, pH 5.3, pH 6.8 and pH 7.4. With respect to non-hygroscopicity, the aforementioned sulphonic acid salts of sibutramine display no increase or decrease in water content when they are exposed to relative humidities of 10%, 75% and 90% for a period of seven days or longer. With respect to stability, the aforementioned sulphonic acid salts of sibutramine do not generate impurities and do not change in content even when they are exposed to a high temperature of 60° C. for a period of one month or longer. The sulphonic acid salts of sibutramine also exhibit good photostability.

The benzenesulfonic acid, camphorsulfonic acid, p-toluenesulfonic acid, ethane disulfonic acid and ethanesulfonic acid, used for preparing the sulphonic acid salts of sibutramine, are organic acids that have been approved for pharmaceutical use by the American FDA, and are typically used in a number of medicaments. Since these acids are less-toxic acids that have been proven safe for long-term use, the novel sulphonic acid salts of sibutramine may be suitable for long-term administration.

Like sibutramine hydrochloride, the sulphonic acid salt of sibutramine according to the present invention, which is a racemic compound, is a roughly 1:1 mixture of optically-pure (+) and (−) enantiomers of a sulphonic acid salt of sibutramine.

The besylate, camsylate, tosylate, edisylate and esylate hemihydrate salts of sibutramine according to the present invention may be crystalline or non-crystalline. Crystalline forms of the sulfonic acid salts of sibutramine are preferred with respect to physical properties such as non-hygroscopicity, thermodynamic stability and flowability.

In detail, sibutramine besylate is characterized by having an X-ray diffraction pattern in which peaks having an intensity of 200 or greater appear at 2θ values of 6.6, 10.9, 13.4, 14.5, 16.2, 17.1, 17.4, 19.7, 20.1 21.4, 22.0, 22.7, 23.5, 24.6, 24.9, 25.7, 26.6, 27.3, and 32.9.

Sibutramine camsylate is characterized by having an X-ray diffraction pattern in which peaks having an intensity of 200 or greater appear at 2θ values of 6.7, 8.1, 12.5, 12.8, 13.3, 15.0, 16.0, 16.6, 18.4, 19.0, 20.0, 21.3, 22.5, 22.8, 24.2, 24.7, 25.0, 26.6, 28.3, and 33.8.

Sibutramine tosylate is characterized by having an X-ray diffraction pattern in which peaks having an intensity of 200 or greater appear at 2θ values of 6.4, 11.0, 11.1, 12.3, 12.8, 14.2, 16.5, 17.1, 19.2, 19.8, 21.3, 22.1, 24.1, 24.9, 26.3, 26.5, and 27.8.

Sibutramine edisylate is characterized by having an X-ray diffraction pattern in which peaks having an intensity of 200 or greater appear at 2θ values of 6.6, 10.2, 11.2, 12.2, 12.8, 13.7, 14.0, 16.4, 18.0, 18.5, 19.2, 19.8, 20.9, 21.3, 22.0, 22.6, 23.7, 24.4, 25.0, 26.5, 27.3, 29.0, and 30.3.

Sibutramine esylate hemihydrate is characterized by having an X-ray diffraction pattern in which peaks having an intensity of 200 or greater appear at 2θ values of 8.0, 10.4, 11.1, 11.7, 12.7, 14.9, 16.0, 16.5, 17.6, 18.0, 18.4, 20.1, 20.8, 22.3, 23.2, 23.4, 23.6, 24.1, 25.0, 25.9, 27.2, 28.6, 30.0, and 33.8.

In anther aspect, the present invention relates to a method of preparing the sulphonic acid salt of sibutramine.

In detail, the present invention includes a method of preparing a sulphonic acid salt of sibutramine, comprising reacting sibutramine with a sulphonic acid selected from among benzenesulfonic acid, camphorsulfonic acid, p-toluenesulfonic acid, ethane disulfonic acid and ethanesulfonic acid in an inert solvent.

In detail, the reaction takes place according to the following Reaction 1.

[Reaction 1]

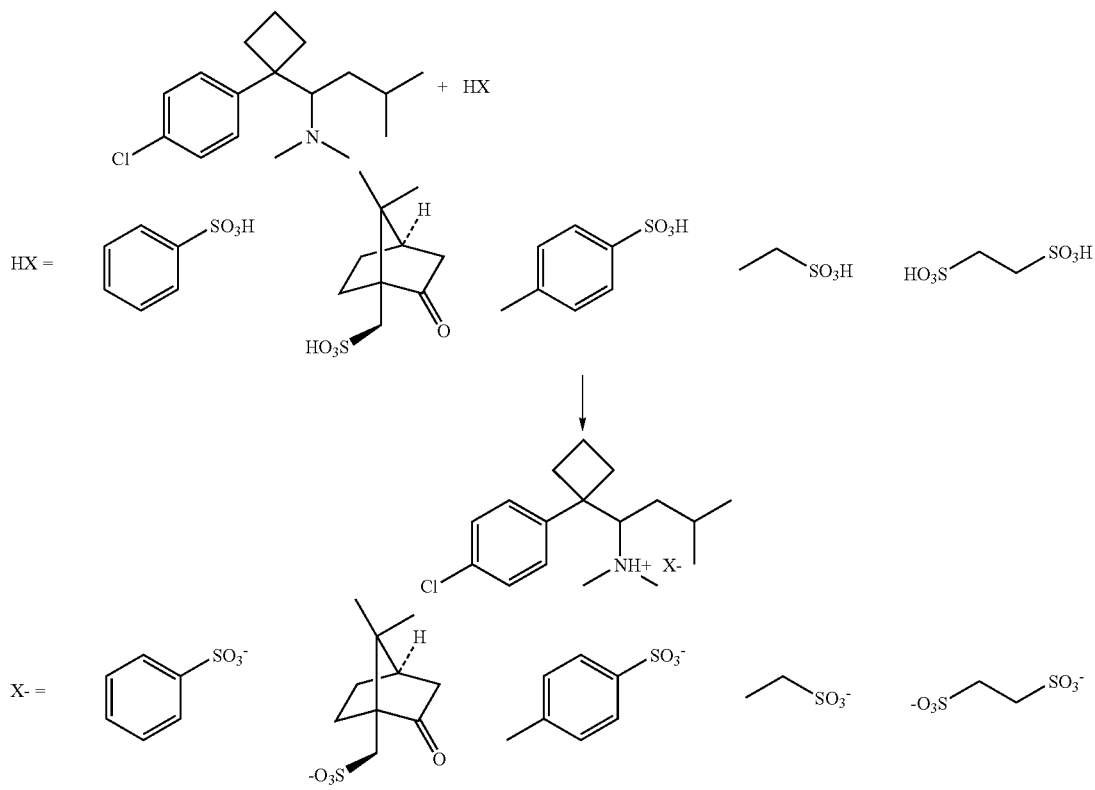

The sibutramine used as a reactant is a 1:1 mixture of (−)-sibutramine and (+)-sibutramine. Among sulphonic acids, camphorsulfonic acid may be a racemic compound or an optically pure substance, and optically pure (+)-(1S)-camphorsulfonic acid is preferred.

The sulphonic acids used in the preparation method of the present invention have been known to have $LD_{50}$ and $LDL_0$ values, as follows: benzenesulfonic acid has an oral-rat $LD_{50}$ of 1,157 mg/kg, camphorsulfonic acid has a subcutaneous-mouse $LD_{50}$ of 2,502 mg/kg, p-toluenesulfonic acid has an oral-rat $LD_{50}$ of 2,480 mg/kg, ethane disulfonic acid has an intravenous-mouse $LDL_0$ of 68 mg/kg, and ethanesulfonic acid has an intravenous-mouse $LDL_0$ of 48 mg/kg. These organic acids have been approved for pharmaceutical use by the American FDA, and have been used in a variety of medicaments. In particular, these acids have been used safely for a long period of time in medicaments having diverse applications, such as anti-hypertensive amlodipine and sultamicillin, tosufloxacin, chlomethiazole and ergotoxin.

The inert solvent available in the preparation method of the present invention includes ethyl acetate, methanol, ethanol, isopropanol, acetonitrile, hexane, isopropyl ether, and t-butyl methyl ether. Ethyl acetate or ethanol is preferred. These inert solvents may be used singly or in combination.

In the inert solvent, one equivalent of sibutramine may be reacted with 1 to 2 equivalents, preferably 1.02 to 1.2 equivalents, of sulphonic acid, at −5 to 40° C., preferably 20 to 30° C., for 0.5 to 5 hours, preferably 1 to 2 hours.

The preparation method of the present invention may provide a sulphonic acid salt of sibutramine in a yield of higher than 90% and a high purity of greater than 99%.

The present invention relates to a pharmaceutical composition comprising a therapeutically effective amount of a sulphonic acid salt of sibutramine and a pharmaceutically acceptable diluent or carrier, and a method of treating or preventing diseases by administering the composition. In an aspect, the present invention includes a pharmaceutical composition for treating or preventing pathological states of obesity and related disorders, comprising a therapeutically effective amount of a sulphonic acid salt of sibutramine and a pharmaceutically acceptable diluent or carrier, and a method of treating or preventing pathological states of obesity and related disorders using this composition.

The present invention also includes a pharmaceutical composition for treating depression, comprising a therapeutically effective amount of a sulphonic acid salt of sibutramine and a pharmaceutically acceptable diluent or carrier, and a method of treating depression by administering this composition.

The present invention further includes a pharmaceutical composition for treating or preventing Parkinson's disease, comprising a therapeutically effective amount of a sulphonic acid salt of sibutramine and a pharmaceutically acceptable diluent or carrier, and a method of treating or preventing Parkinson's disease by administering this composition.

The present invention still further includes a pharmaceutical composition for treating insulin-independent diabetes mellitus, comprising a therapeutically effective amount of a sulphonic acid salt of sibutramine and a pharmaceutically acceptable diluent or carrier, and a method of treating insulin-independent diabetes mellitus by administering this composition.

The present invention still further includes a pharmaceutical composition for treating epilepsy, comprising a therapeutically effective amount of a sulphonic acid salt of sibutramine and a pharmaceutically acceptable diluent or carrier, and a method of treating epilepsy by administering this composition.

The pharmaceutical composition comprising the sulphonic acid salt of sibutramine according to the present invention as an active ingredient may be preferably administered orally, for example in the form of tablets or capsules.

Tablets may be prepared by mixing an active ingredient with a carrier, a diluent or an excipient and compressing the mixture into tablets. Examples of suitable carriers, diluents or excipients include disintegrators such as starch, sugars and mannitol; fillers and extenders such as calcium phosphate and silicic derivatives; binding agents such as carboxymethyl cellulose and other cellulose derivatives, gelatin and polyvinyl pyrrolidone; and lubricants such as talc, calcium and magnesium stearate, and solid polyethylene glycol. Also, hard or soft gelatin capsules containing an active ingredient, either with or without an additive such as the carriers, diluents or excipients may be prepared according to an ordinary method.

The pharmaceutical composition preferably contains a crystalline sulphonic acid salt of sibutramine, represented by Chemical Formula 1, as an active ingredient in an amount of 1 to 50 parts by weight based on 250 parts by weight of the composition. For example, the pharmaceutical composition having a total weight of 250 mg according to the present invention may be prepared in such a manner as to contain 10 mg (based on sibutramine content) of the crystalline sulphonic acid salt of sibutramine, represented by Chemical Formula 1, 115 mg of microcrystalline cellulose, 115 mg of lactose, 5 mg of silicon dioxide, and 5 mg of magnesium stearate. However, this composition of the pharmaceutical composition is illustrative, and thus, the scope of the present invention is not limited thereto.

A better understanding of the present invention may be obtained through the following examples which are set forth to illustrate, but are not to be construed as the limit of the present invention.

EXAMPLES

Besylate, camsylate, tosylate, edisylate and esylate hemihydrate salts of sibutramine were prepared according to the preparation method of the present invention, and were compared with sibutramine hydrochloride hydrate for physical properties including hygroscopicity, solubility, stability, light stability and crystallizability. In addition, the sulphonic acid salts of sibutramine were formulated into capsules in order to examine their formulability and release patterns.

Reference Example 1

Preparation of Sibutramine Hydrochloride Monohydrate

Sibutramine hydrochloride anhydrate was prepared according to a method described in Korean Pat. Publication No. 90-00274. Then, according to a method described in Korean Pat. Publication No. 94-08913, 10 g of the prepared sibutramine hydrochloride anhydrate was dissolved in a boiling mixture of 110 ml acetone and 1.2 ml water, and the resulting solution was hot-filtered and distilled to remove 80 ml of the solvent, thus reducing the volume of the filtrate. The concentrate was filtered to recover a generated solid. The solid was vacuum-dried, thus obtaining 9.2 g (yield: 87%) of the compound of Chemical Formula 2, which had a melting point of 195° C.

Example 1

Preparation of Sibutramine Besylate

Sibutramine (22.4 g, 0.08 mol) was dissolved in 224 ml of ethyl acetate with agitation. After the solution was adjusted to 25° C., benzenesulfonic acid (12.64 g, 0.08 mol) in 124 ml ethyl acetate was slowly added in droplets to the solution. The resulting mixture was agitated at 25° C. for 2 hrs to form precipitates and then agitated at 4° C. for 1 hr. The generated solid was recovered by filtration under pressure, washed with 100 ml of ethyl acetate, and vacuum-dried at 40° C., thus obtaining 33.99 g (yield: 97.0%) of a target compound.

The obtained sibutramine besylate was subjected to elemental analysis and melting point analysis, and the results are as follows.

TABLE 1

| Elemental analysis ($C_{23}H_{32}ClNO_3S$) | Unit (%) |
|---|---|
| Measured value | C: 62.98, H: 7.48, N: 3.20, O: 11.24, S: 7.34 |
| Theoretical value | C: 63.07, H: 7.36, N: 3.20, O: 10.96, S: 7.32 |

Melting point: 187° C.

NMR (δ, DMSO-$d_6$): 8.42 (1H, s), 7.63~7.32 (9H, m), 3.76 (1H, t), 2.83 (3H, d), 2.55~2.50 (1H, d), 2.32~2.30 (2H, m), 2.13 (3H, d), 1.90 (1H, m), 1.69 (2H, m), 1.41 (2H, m), 0.99 (6H, t)

Example 2

Preparation of Sibutramine Camsylate

Sibutramine (30.0 g, 0.107 mol) was dissolved in 300 ml of ethyl acetate with agitation. After the solution was adjusted to 25° C., (1S)-(+)-camphor-10-sulfonic acid (24.9 g, 0.107 mol) in 250 ml ethyl acetate was slowly added in droplets to the solution. The resulting mixture was agitated at 25° C. for 2 hrs to form precipitates and then agitated at 4° C. for 1 hr. The generated solid was recovered by filtration under pressure, washed with 100 ml of ethyl acetate, and vacuum-dried at 40° C., thus obtaining 52.31 g (yield: 95.4%) of a target compound.

The obtained sibutramine camsylate was subjected to elemental analysis and melting point analysis, and the results are as follows.

TABLE 2

| Elemental analysis ($C_{27}H_{42}ClNO_4S$) | Unit (%) |
|---|---|
| Measured value | C: 63.51, H: 8.42, N: 2.80, O: 12.71, S: 6.44 |
| Theoretical value | C: 63.32, H: 8.27, N: 2.73, O: 12.50, S: 6.26 |

Melting point: 190° C.

NMR (δ, DMSO-$d_6$): 8.49 (1H, s), 7.56~7.49 (4H, m), 3.76 (1H, t), 2.87 (1H, d), 2.83 (3H, d), 2.75 (1H, t), 2.55~2.50 (1H, d), 2.39 (1H, d), 2.32~2.20 (3H, m), 2.13 (3H, d), 1.95~1.70 (6H, m), 1.50~1.28 (4H, m), 1.06 (3H, s), 0.99 (6H, t), 0.76 (3H, s)

Example 3

Preparation of Sibutramine Tosylate

Sibutramine (22.4 g, 0.08 mol) was dissolved in 224 ml of ethyl acetate with agitation. After the solution was adjusted to 25° C., p-toluenesulfonic acid monohydrate (15.2 g, 0.08 mol) in 160 ml ethyl acetate was slowly added in droplets to the solution. The resulting mixture was agitated at 25° C. for 2 hrs to form precipitates and then agitated at 4° C. for 0.1 hr. The generated solid was recovered by filtration under pressure, washed with 100 ml of ethyl acetate, and vacuum-dried at 40° C., thus obtaining 35.14 g (yield: 97.1%) of a target compound.

The obtained sibutramine tosylate was subjected to elemental analysis and melting point analysis, and the results are as follows.

TABLE 3

| Elemental analysis ($C_{24}H_{34}ClNO_3S$) | Unit (%) |
| --- | --- |
| Measured value | C: 64.14, H: 7.63, N: 3.10, O: 10.76, S: 7.39 |
| Theoretical value | C: 63.77, H: 7.58, N: 3.10, O: 10.62, S: 7.09 |

Melting point: 185° C.

NMR (δ, DMSO-$d_6$): 8.42 (1H, s), 7.54~7.48 (6H, m), 7.13 (2H, d), 3.76 (1H, t), 2.83 (3H, d), 2.50 (1H, d), 2.32~2.30 (2H, m), 2.30 (3H, d), 2.13 (3H, d), 1.90 (1H, m), 1.69 (2H, m), 1.39 (2H, m), 0.99 (6H, t)

Example 4

Preparation of Sibutramine Edisylate

Sibutramine (24.0 g, 0.086 mol) was dissolved in 240 ml of ethyl acetate with agitation. After the solution was adjusted to 25° C., 1,2-ethane disulfonic acid (8.16 g, 0.043 mol) in 72 ml ethyl acetate was slowly added in droplets to the solution. The resulting mixture was agitated at 25° C. for 2 hrs to form precipitates and then agitated at 4° C. for 1 hr. The generated solid was recovered by filtration under pressure, washed with 100 ml of ethyl acetate, and vacuum-dried at 40° C., thus obtaining 27.40 g (yield: 85.0%) of a target compound. The obtained sibutramine edisylate was subjected to elemental analysis and melting point analysis, and the results are as follows.

TABLE 4

| Elemental analysis ($C_{36}H_{58}Cl_2N_2O_6S_2$) | Unit (%) |
| --- | --- |
| Measured value | C: 57.62, H: 7.78, N: 3.72, O: 13.50, S: 8.66 |
| Theoretical value | C: 57.66, H: 7.80, N: 3.74, O: 12.80, S: 8.55 |

Melting point: 270° C.

NMR (δ, DMSO-$d_6$): 8.51 (1H, s), 7.55~7.49 (4H, m), 3.76 (1H, t), 2.83 (3H, d), 2.68 (2H, s), 2.50 (2H, d), 2.32 (2H, t), 2.13 (3H, d), 1.90 (1H, m), 1.69 (2H, m), 1.39 (2H, m), 0.99 (6H, t)

Example 5

Preparation of Sibutramine Esylate Hemihydrate

Sibutramine (20.0 g, 0.071 mol) was dissolved with agitation in a mixture of 80 ml of ethyl acetate, 80 ml of t-butyl methyl ether and 2 ml of distilled water. After the solution was adjusted to 25° C., ethanesulfonic acid (8.68 g, 0.078 mol) was slowly added in droplets to the solution. The resulting mixture was agitated at 25° C. for 2 hrs to form precipitates and then agitated at 4° C. for 1 hr. The generated solid was recovered by filtration under pressure, washed with 100 ml of ethyl acetate, and vacuum-dried at 40° C., thus obtaining 26.0 g (yield: 93.9%) of a target compound.

The obtained sibutramine esylate hemihydrate was subjected to elemental analysis and melting point analysis, and the results are as follows.

TABLE 5

| Elemental analysis ($C_{19}H_{32}ClNO_3S$-½$H_2O$) | Unit (%) |
| --- | --- |
| Measured value | C: 57.44, H: 8.42, N: 3.63, O: 13.76, S: 8.28 |
| Theoretical value | C: 57.20, H: 8.34, N: 3.51, O: 14.03, S: 8.04 |

Melting point: 174° C.

NMR (δ, DMSO-$d_6$): 8.53 (1H, s), 7.55~7.48 (4H, m), 3.76 (1H, t), 2.83 (3H, d), 2.51 (2H, d), 2.42 (2H, q), 2.33 (2H, m), 2.13 (3H, t), 1.90 (1H, m), 1.69 (2H, m), 1.39 (2H, m), 1.08 (3H, t), 0.99 (6H, t)

Example 6

Preparation of Capsules Containing Sibutramine Besylate

Ingredients were mixed according to the composition described in Table 6, below, to prepare capsules containing sibutramine besylate.

TABLE 6

| Ingredients | Content (per capsule) |
| --- | --- |
| Sibutramine besylate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 7

Preparation of Capsules Containing Sibutramine Camsylate

Ingredients were mixed according to the composition described in Table 7, below, to prepare capsules containing sibutramine campsylate.

TABLE 7

| Ingredients | Content (per capsule) |
|---|---|
| Sibutramine camsylate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 8

Preparation of Capsules Containing Sibutramine Tosylate

Ingredients were mixed according to the composition described in Table 8, below, to prepare capsules containing sibutramine tosylate.

TABLE 8

| Ingredients | Content (per capsule) |
|---|---|
| Sibutramine tosylate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 9

Preparation of Capsules Containing Sibutramine Edisylate

Ingredients were mixed according to the composition described in Table 9, below, to prepare capsules containing sibutramine edisylate.

TABLE 9

| Ingredients | Content (per capsule) |
|---|---|
| Sibutramine edisylate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 10

Preparation of Capsules Containing Sibutramine Esylate Hemihydrate

Ingredients were mixed according to the composition described in Table 10, below, to prepare capsules containing sibutramine esylate hemihydrate.

TABLE 10

| Ingredients | Content (per capsule) |
|---|---|
| Sibutramine esylate hemihydrate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 11

Evaluation of Hygroscopicity of the Sulphonic Acid Salts of Sibutramine

The sulphonic acid salts of sibutramine, prepared in Examples 1 to 5, and sibutramine hydrochloride monohydrate were exposed to humid conditions (10%, 75% and 90% RH) at 25° C. for a period of three days or one week. Then, the water content (K.F. water %) of the samples was measured. The results are given in Table 11, below.

TABLE 11

| Storage humidity (relative humidity, %) | | 10% | | 75% | | 90% | |
|---|---|---|---|---|---|---|---|
| Storage period | Initial | 3 days | 1 week | 3 days | 1 week | 3 days | 1 week |
| Bensylate | 0.02% | 0.02% | 0.02% | 0.02% | 0.05% | 0.05% | 0.05% |
| Camsylate | 0.09% | 0.09% | 0.08% | 0.06% | 0.06% | 0.08% | 0.12% |
| Tosyalte | 0.10% | 0.08% | 0.07% | 0.05% | 0.08% | 0.05% | 0.07% |
| Edisylate | 0.05% | 0.06% | 0.05% | 0.04% | 0.05% | 0.04% | 0.05% |
| Esylate hemihydrate | 2.37% | 2.35% | 2.37% | 2.29% | 2.35% | 2.44% | 2.40% |
| HCl monohydrate | 5.50% | 5.51% | 5.48% | 5.49% | 5.50% | 5.50% | 5.49% |

As shown in Table 11, besylate, camsylate, tosylate, edisylate and esylate hemihydrate salts of sibutramine, like sibutramine hydrochloride monohydrate, exhibited almost no change in water content under humid conditions.

Example 12

Evaluation of Solubility of the Sulphonic Acid Salts of Sibutramine

The sulphonic acid salts of sibutramine, prepared in Examples 1 to 5, and sibutramine hydrochloride monohydrate were evaluated for solubility in aqueous solutions having various pH values. The results are given in Table 12, below.

TABLE 12

| Novel salts | Solvents | | | | | |
|---|---|---|---|---|---|---|
| | DW | pH 1.2 | pH 4.0 | pH 5.3 | pH 6.8 | pH 7.4 |
| Besylate | 19.18 | 15.18 | 8.51 | 5.72 | 21.86 | 7.01 |
| Camsylate | 23.67 | 16.18 | 16.75 | 7.45 | 29.83 | 13.97 |
| Tosylate | 24.32 | 8.36 | 7.56 | 5.53 | 21.92 | 7.69 |
| Edisylate | 25.98 | 10.57 | 9.78 | 5.68 | 19.44 | 8.04 |
| Esylate hemihydrate | 84.10 | 70.65 | 26.42 | 19.53 | 69.42 | 27.61 |
| HCl monohydrate | 26.18 | 13.36 | 9.58 | 6.58 | 23.14 | 9.2 |

As shown in Table 12, in distilled water (DW) and buffer solutions at various pH values, besylate, tosylate and edisylate salts of sibutramine had a slightly low solubility compared to sibutramine hydrochloride monohydrate, but this solubility was higher than the solubility (3 mg/ml) sufficient for preparing pharmaceutical formulations such as capsules. Sibutramine camsylate exhibited a solubility similar to that of sibutramine hydrochloride monohydrate. Sibutramine esylate hemihydrate displayed excellent solubility compared to sibutramine hydrochloride monohydrate. In addition, when the five sulphonic acid salts of sibutramine were formulated into capsules and evaluated for release rates, they all generated the same results as did sibutramine hydrochloride monohydrate.

Example 13

Evaluation of Stability of the Sulphonic Acid Salts of Sibutramine

The sulphonic acid salts of sibutramine, prepared in Examples 1 to 5, and sibutramine hydrochloride monohydrate were exposed to a stringent 60° C. heat treatment. The results are summarized in Table 13, below.

TABLE 13

| Salts of sibutramine | Storage period | | | |
|---|---|---|---|---|
| | Initial | 1 wk | 2 wks | 4 wks |
| Besylate | 1.000 | 1.000 | 0.999 | 1.000 |
| Camsylate | 1.000 | 1.000 | 0.999 | 0.999 |
| Tosylate | 1.000 | 0.999 | 1.000 | 0.999 |

TABLE 13-continued

| Salts of sibutramine | Storage period | | | |
|---|---|---|---|---|
| | Initial | 1 wk | 2 wks | 4 wks |
| Edisylate | 1.000 | 0.999 | 1.000 | 0.999 |
| Esylate hemihydrate | 1.000 | 1.000 | 0.999 | 0.999 |
| HCl monohydrate | 1.000 | 0.999 | 0.999 | 0.999 |

HPLC was performed under the following conditions.
Wavelength of UV detection: 225 nm
Column: octadecyl silica gel, C18 (4.6×150 mm, 5 μm)
Mobile phase: an aqueous solution of ammonium phosphate monohydride (0.05 M) (adjusted to pH 6 with phosphoric acid): acetonitrile=35:65
Flow rate: 1.0 ml/min As shown in Table 13, like sibutramine hydrochloride monohydrate, the sulphonic acid salts of sibutramine displayed almost no change in content upon the stringent 60° C. heat treatment. These results indicate that the sulphonic acid salts of sibutramine, like sibutramine hydrochloride monohydrate, have good chemical stability at high temperature.

Example 14

Evaluation of Light Stability of the Sulphonic Acid Salts of Sibutramine

A light stability test was performed as follows. The sulphonic acid salts of sibutramine, prepared in Examples 1 to 5, and sibutramine hydrochloride monohydrate were exposed to fluorescence at 25° C. using a light stability test chamber suitable for the ICH guideline, for storage periods of 1, 2 and 4 weeks. The results are given in Table 14, below.

TABLE 14

| Salts of sibutramine | Storage period | | | |
|---|---|---|---|---|
| | Initial | 1 wk | 2 wks | 4 wks |
| Besylate | 1.000 | 1.000 | 0.999 | 0.999 |
| Camsylate | 1.000 | 0.999 | 1.000 | 0.999 |
| Tosylate | 1.000 | 1.000 | 0.999 | 0.999 |
| Edisylate | 1.000 | 1.000 | 0.999 | 1.000 |
| Esylate hemihydrate | 1.000 | 0.999 | 1.000 | 0.999 |
| HCl monohydrate | 1.000 | 0.999 | 1.000 | 0.999 |

As shown in Table 14, when content changes of the sulphonic acid salts of sibutramine were analyzed by HPLC in order to determine the light stability thereof, the sulphonic acid salts of sibutramine, like sibutramine hydrochloride monohydrate, displayed good light stability.

INDUSTRIAL APPLICABILITY

The besylate, camsylate, tosylate, edisylate and esylate hemihydrate salts of sibutramine according to the present invention have good physicochemical properties including non-hygroscopicity, solubility, stability, formulability and crystallizability. These sulphonic acid salts of sibutramine do not require an additional procedure for preparing a hydrate, and sibutramine esylate hemihydrate exhibits greatly enhanced solubility compared to sibutramine hydrochloride monohydrate. Therefore, the besylate, camsylate, tosylate, edisylate and esylate hemihydrate salts of sibutramine according to the present invention have the following advantages: they are prepared by a simple process, are suitable for long-term storage, guarantee consistency suitable for the preparation of pharmaceutical dosage forms, and have enhanced bioavailability.

Moreover, since the benzenesulfonic, camphorsulfonic, p-toluenesulfonic, ethane disulfonic and ethanesulfonic acids used in the preparation of the novel sulphonic acid salts of sibutramine are less-toxic acids that have been proven to be pharmaceutically safe for long-term use, the novel sulphonic acid salts of sibutramine may be suitable for long-term administration with no risk of toxicity.

The invention claimed is:

1. A sulphonic acid salt of sibutramine, which has a structure of the following Chemical Formula 1:

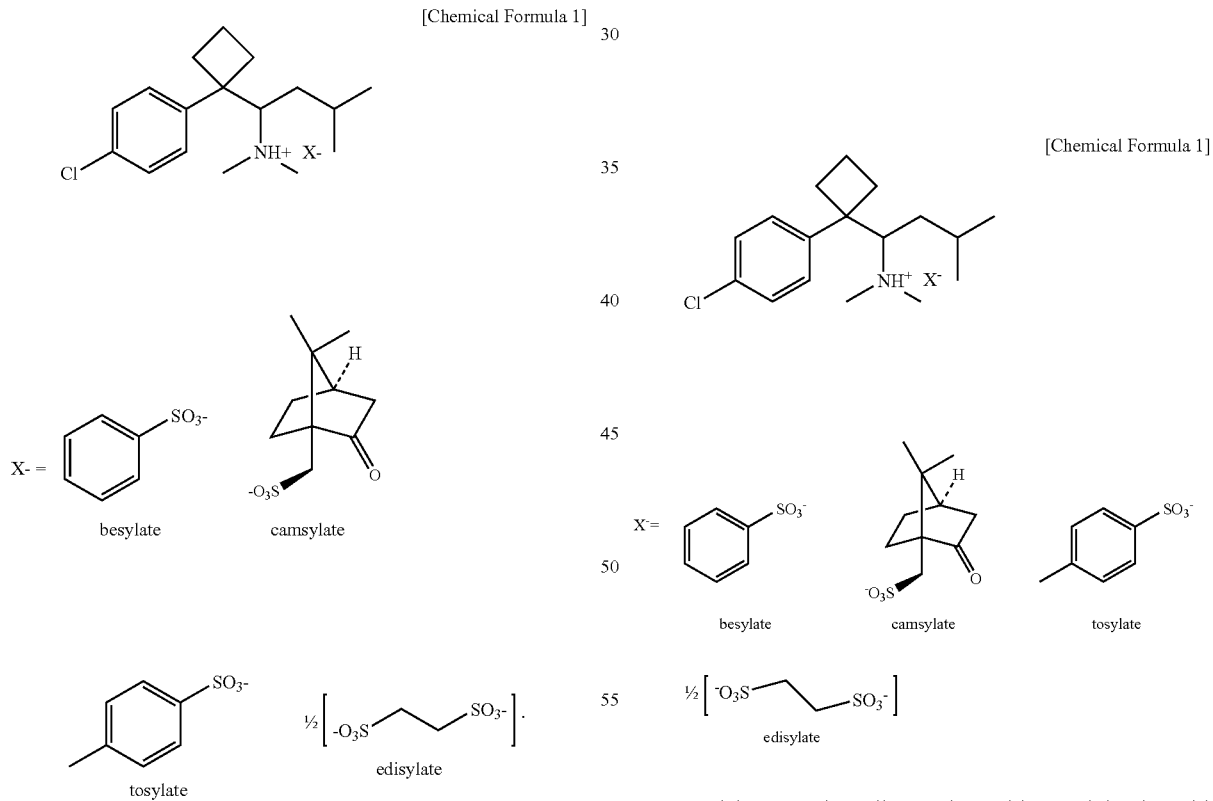

2. The sulphonic acid salt of sibutramine as set forth in claim 1, which is sibutramine besylate having an X-ray diffraction pattern in which peaks having an intensity of 200 or greater appear at 2θ values of 6.6, 10.9, 13.4, 14.5, 16.2, 17.1, 17.4, 19.7, 20.1 21.4, 22.0, 22.7, 23.5, 24.6, 24.9, 25.7, 26.6, 27.3, and 32.9.

3. The sulphonic acid salt of sibutramine as set forth in claim 1, which is sibutramine camsylate having an X-ray diffraction pattern in which peaks having an intensity of 200 or greater appear at 2θ values of 6.7, 8.1, 12.5, 12.8, 13.3, 15.0, 16.0, 16.6, 18.4, 19.0, 20.0, 21.3, 22.5, 22.8, 24.2, 24.7, 25.0, 26.6, 28.3, and 33.8.

4. The sulphonic acid salt of sibutramine as set forth in claim 1, which is sibutramine tosylate having an X-ray diffraction pattern in which peaks having an intensity of 200 or greater appear at 2θ values of 6.4, 11.0, 11.1, 12.3, 12.8, 14.2, 16.5, 17.1, 19.2, 19.8, 21.3, 22.1, 24.1, 24.9, 26.3, 26.5, and 27.8.

5. The sulphonic acid salt of sibutramine as set forth in claim 1, which is sibutramine edisylate having an X-ray diffraction pattern in which peaks having an intensity of 200 or greater appear at 2θ values of 6.6, 10.2, 11.2, 12.2, 12.8, 13.7, 14.0, 16.4, 18.0, 18.5, 19.2, 19.8, 20.9, 21.3, 22.0, 22.6, 23.7, 24.4, 25.0, 26.5, 27.3, 29.0, and 30.3.

6. A method of preparing the sulphonic acid salt of sibutramine represented by the following Chemical Formula 1:

comprising reacting sibutramine with a sulphonic acid selected from among benzenesulfonic acid, camphorsulfonic acid, p-toluenesulfonic acid, and ethane disulfonic acid in an inert solvent.

7. A pharmaceutical composition comprising a sulphonic acid salt of sibutramine represented by the following Chemical Formula 1:

[Chemical Formula 1]

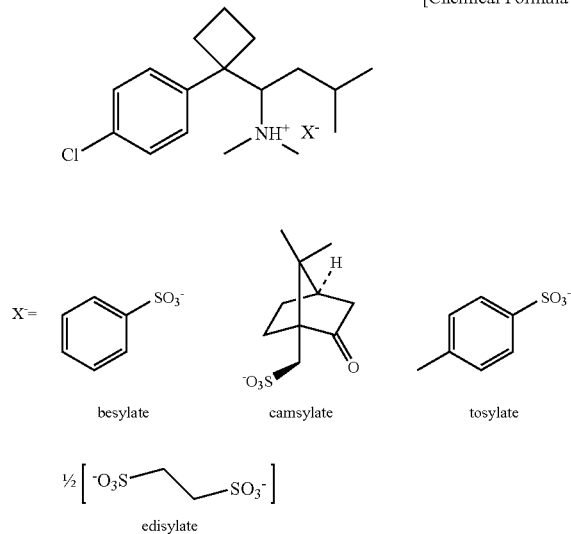

and a pharmaceutically acceptable diluent or carrier.

8. The pharmaceutical composition as set forth in claim 7, which is formulated into tablets or capsules.

9. A method of treating obesity, depression, Parkinson's disease, insulin-independent diabetes mellitus or epilepsy, comprising administering a pharmaceutical composition comprising a sulphonic acid salt of sibutramine represented by the following Chemical Formula 1:

[Chemical Formula 1]

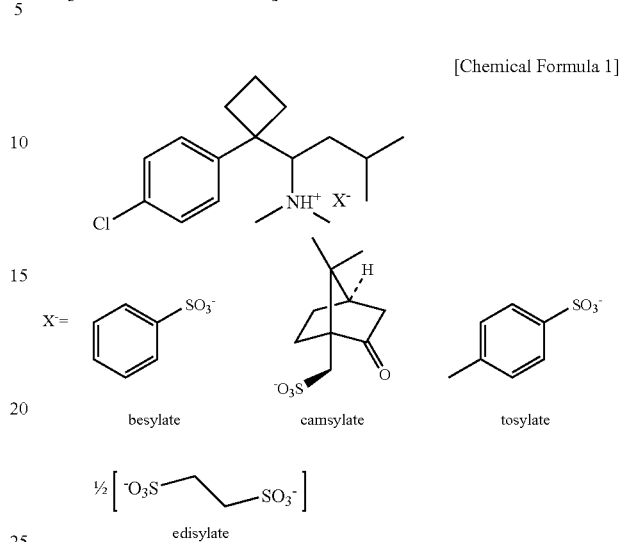

10. The pharmaceutical composition as set forth in claim 7, wherein the composition is for treating obesity, depression, Parkinson's disease, insulin-independent diabetes mellitus, or epilepsy.

* * * * *